United States Patent
Welzel

(10) Patent No.: US 6,740,672 B1
(45) Date of Patent: May 25, 2004

(54) USE OF 5HT$_3$-RECEPTOR ANTAGONISTS FOR THE TREATMENT OF CHRONIC FATIGUE SYNDROME

(75) Inventor: Dieter Welzel, Nuremberg (DE)

(73) Assignee: Novartis Pharma GmbH (DE)

( * ) Notice: Subject to any disclaimer, the term of this patent is extended or adjusted under 35 U.S.C. 154(b) by 0 days.

(21) Appl. No.: 09/868,972

(22) PCT Filed: Dec. 22, 1999

(86) PCT No.: PCT/DE99/04071

§ 371 (c)(1),
(2), (4) Date: Sep. 4, 2001

(87) PCT Pub. No.: WO00/37073

PCT Pub. Date: Jun. 29, 2000

(30) Foreign Application Priority Data

Dec. 22, 1998 (DE) ......................................... 198 59 406

(51) Int. Cl.⁷ .................. A61K 31/4178; A61K 31/437; A61K 31/439

(52) U.S. Cl. ........................ 514/397; 514/305; 514/304; 514/292

(58) Field of Search ................................ 514/397, 305, 514/304, 292

(56) References Cited

U.S. PATENT DOCUMENTS 5,614,523 A * 3/1997 Audia et al. ................. 514/252

* cited by examiner

Primary Examiner—Phyllis G. Spivack
(74) Attorney, Agent, or Firm—Bachman & LaPointe, P.C.

(57) ABSTRACT

5HT$_3$-receptor-antagonists for the treatment of CFS (Chronic Fatigue Syndrome) are disclosed.

9 Claims, No Drawings

USE OF 5HT$_3$-RECEPTOR ANTAGONISTS FOR THE TREATMENT OF CHRONIC FATIGUE SYNDROME

The present invention relates to a new use for 5HT$_3$-receptor-antagonists. CFS, chronic fatigue syndrome, was defined as a diagnostic entity at the end of the eighties and has been the subject of numerous studies and publications. Particularly problematic with respect to the diagnosis of CFS is the fact that a complex of symptoms of a pathological fatigue and susceptibility to fatigue is present, wherein the present symptoms are at least partially also to be encountered in a number of other internistic and psychiatric illnesses.

Thus, one must note the absence of symptoms, other than those which can be attributed to other illnesses, useful when diagnosing CFS.

Principally there is the question of what fatigue actually is. Generally, it is referred to as a physiological lack of capability, but may also be felt as lack of drive, lack of stamina in and physical weakness. Mental fatigue can be divided into a bad ability to concentrate and remember, lack of interest in activities and sleepiness throughout the day.

On the other hand fatigue is a natural phenomenon occurring after physical or psychological stress which goes away after resting or sleeping. Thus, the differentiation between "normal" and "abnormal" fatigue is of importance. It is helpful to note that patients suffering from CFS usually also suffer from further symptoms which can be employed for diagnosis.

Since comparatively short term conditions of fatigue may occur during or after an illness or under strong and lasting stress, one concludes the presence of CFS as chronic illness only on the occasion of symptoms persisting for at least six months.

Generally, the presence of CFS is determined in a patient in whom the fatigue is medically not explainable even after careful clinical investigation. It is generally acknowledged that patients with a defined organic illness are to be excluded from the group of CFS patients. With respect to psychological illnesses, there is less agreement in relation to a corresponding exclusion. Some scientists are of the opinion that patients suffering from depression and anxiety should be excluded since an appropriate explanation for the fatigue in these patients is present. Other scientists are of a different opinion.

In the presence of CFS, symptoms of a chronic mental and physical fatigue usually occur which grow worse with activity and are often accompanied by pain in the muscles. In this respect, patients frequently report that they are fit and capable for a short period of time, but then suffer from heavy fatigue for hours or days. Further symptoms that ordinarily are reported include non-relaxing sleep, dizziness and breathlessness as well as head aches and further symptoms. Depressive periods and conditions of anxiety also occur in part of the patients. The diagnosis of CFS is therefore always a diagnosis by means of exclusion.

Until now no effective way of treatment could be found for treating CFS. Frequently antidepressants are employed for therapy, but a first comprehensive, randomized placebo-controlled investigation on antidepressants was negative in result (Vercoulen, Jan H. M. M. et al., Lancet 1996, 347:858–61). The subject of the referenced investigation was fluoxetin, wherein in the end not even patients with accompanying symptoms of depression showed a positive result in response to a daily dose of 20 mg fluoxetin. This already points out a specific pathogenesis of CFS in contrast to depressive illnesses.

Studies indicate there are concrete indications for serotonic activity in the brain, such as is shown by the significantly increased rise of prolactin in the serum after an acute application of D-Feufluoroamin on patients with CFS.

Studies have become known according to which there are concrete indications for a serotonic activity in the brain, as the significantly increased rise of prolactin in the serum after an acute application of D-Feufluoroamin on patients with CFS shows.

It is generally to be noticed that indications of a convenient and effective therapy for the treatment of CFS are lacking.

It is object of the present invention to provide compounds that are suitable for the manufactured of drugs for the treatment of CFS.

The present object is achieved by the features of claim 1. Advantageous embodiments of the invention form the subject matter of the depending claims.

The present invention is based on the finding that the use of antidepressants with CFS which amplify the action of serotonin is not appropriate, which is also evidenced by the cited study with respect to fluoxetin. First, this is a turn away from therapeutic methods that were customary until now and which essentially were focussed on the presence of depressive conditions. Thus, the use of substances is suggested which reduces the effect of serotonin and which are canalized by the subgroup of the so called 5HT$_3$-receptors. According to tile invention, the pharmacologically known class of the highly specific 5HT3-receptor-antagonists, which for example find application in the treatment of the emesis in the chemotherapy of cancer, are suited for this purpose.

In an advantageous embodiment of the present invention Alosetron, Tropisetron, Ondansetron, Granisetron, Bemesetron or combinations of at least two of the foregoing, very selective acting substances are employed as 5HT$_3$-receptor-antagonists. In this respect it is preferred that the amount of active substance in one dosage unit amounts to 2 to 10 mg, an amount of 5 to 8 mg active substance in one dosage unit being especially preferred. A daily dosage comprises generally an amount of active substance of 2 to 20 mg, particularly preferred is an amount of active substance of 5 to 16 mg. If necessary, those skilled in the art also know how to vary the active substance in a dosage unit or the level of the daily dosage according to the requirements. The factors determining this, such as body weight, overall constitution, response to the treatment and the like will constantly be monitored by the artisan in order to be able to react accordingly and adjust the amount of active substance in a dosage unit or to adjust the daily dosage if necessary.

Preferably, the substances that are used for producing the drug according to the invention, 5HT$_3$, receptor-antagonists, are processed to an oral or intravenous form of administration to provide possibilities for variation in the application and for providing a possibly most gentle administration for the respective patient.

In the following, the present invention is further illustrated by the way of examples. These examples serve to illustrate and by no means to restrict the scope of the present invention.

To revise the effectiveness of the inventive therapeutic approach two groups of patients of ten patients were treated with Tropisetron and Ondansetron, respectively.

In the preceding diagnostic the Chronic Fatigue Syndrom (CFS) was confined by criteria of classification based on those of the Center of Disease Control and Prevention, in the edition revised 1994 (Fukuda K. et al., Ann Intern Med.

1994, 121:953—1959). In the judgement it was set off from a clinically proven etiologically unclear, persisting or relapsing fatigue (duration >6 months) that has commenced newly or timely delimited (not already existing for life), which is not the consequence of a still lasting overload that does not improve with rest and which leads two a considerable reduction of the earlier level of activity in education and profession as well as in social and personal areas. Prerequisite is that the occurrence of four or more of the following symptoms which, all have had to exist persisting or relapsing for at least six consecutive months of illness and which may not have preceded the fatigue. These symptoms are:

- restriction of the short term memory or concentration severe enough to cause a substantial reduction of the earlier level of activity
- a sore throat (Pharyngitis without pus)
- axillary and lymph nodes of the neck reacting with pain on pressure
- muscle pain
- arthralgia
- headaches of a new quality
- no relaxation by sleep
- worsening of condition for more than 24 hours after efforts.

By such diagnosis of exclusion according to the foregoing criteria a group of patients may be confined the prevalence of which is lying at about 3% and whose discomforts may not be named differently. The group of patients treated with Tropisetron received the active substance in the form of a capsule with an amount of active substance of 5 mg/dosage unit, wherein the daily dosage was also 5 mg. The second group of patients received the active substance Ondansetron in form of tablets, wherein a dosage unit contained 8 mg active substance and the daily dosage consisted of twice a dosage unit, i.e. 16 mg daily.

The administration of the $5HT_3$-receptor-antagonists took place for over 15 days, respectively. During the study patients were monitored for the parameters listed as follows:

- MARDS; days 0 and 15
- VAS (Visual Analog Scale) susceptibility to fatigue/fatigue; days 0, 8 and 15
- VAS fitness; days 0, 8 and 15
- daily recording of both of the VAS by the patient himself
- accompanying symptoms; days 0, 8 and 15
- fitness during the test; day 15
- final evaluation by physician and patient; day 15

The essential changes under therapy were recorded by visual analog scales that documented the extent of the abnormal susceptibility to fatigue/fatigue as well as the reduction of fitness. In this respect the subjectively felt condition for susceptibility to fatigue/fatigue or fitness were marked on a scale comprising a range from 0 to 100, wherein 0 means normal susceptibility to fatigue/fatigue or fitness and 100 for the heaviest susceptibility to fatigue/fatigue or for a 100% reduction in fitness.

With respect to two visual analog scales a significant improvement in an amount of more than 35% could be determined in one third of the patients. This related to both of the groups of the patients similarly. Additionally, considering the patients reporting of a pronounced improvement the response rate amounts to about 66%.

The conducted studies show unambiguously that a pronounced improvement in about a third of the patients occurred with regard to the main symptoms of CFS, fatigue and reduction of fitness, a further third feeling at least a minor improvement with respect to the discomforts. Clinically this is a very significant success in therapy, particularly on the background that other therapeutic approaches have proven to be practically without effect.

Another important indication for the therapy of CFS with respect to the effect of the suggested therapy is the fact that in the studies described herein before a significant improvement of the condition of the patients could be noted within the duration of the study of 15 days which is very surprising in view of the persistence of the determined symptoms, since the diagnostic symptoms had to be present for more than 6 months according to the definition.

The effect of the substances employed in the study, Tropisetron and Ondansetron, on the inhibition of the $5HT_3$-receptor as the common highly specific principle of action is based on the only common feature of the presence of a structural element in form of a indol cycle, since these two compounds differ considerably in their chemical structure.

What is claimed is:

1. A method of treatment for Chronic Fatigue Syndrome (CFS) comprising reducing the effect of serotonin by administering a dosage unit comprised of a $5HT_3$-receptor-antagonist in an amount effective to decrease the effect of serotonin, wherein the $5HT_3$-receptor-antagonists is selected from the group consisting of Alosetron, Tropisetron, Ondansetron, Granisetron, Bemesetron, and mixtures thereof.

2. The method of claim 1, wherein said administering step comprises administering said $5HT_3$-receptor-antagonist in an amount of 2 to 10 mg.

3. The method of claim 2, wherein said amount of said $5HT_3$-receptor-antagonist contained in said dosage unit is 5 to 8 mg.

4. The method of claim 1, wherein said administering step comprises administering a daily dosage of said $5HT_3$-receptor antagonist in an amount from 2 to 20 mg.

5. The method of claim 4, wherein said daily dosage of said $5HT_3$-receptor-antagonist comprises an amount of said $5HT_3$-receptor-antagonist from 5 to 16 mg.

6. The method of claim 1, wherein said $5HT_3$-receptor-antagonist is administered orally.

7. The method of claim 1, wherein said administering said dosage unit comprises administering said dosage unit comprising Tropisetron.

8. The method of claim 7, wherein said administering said dosage unit comprises administering said dosage unit comprising Tropisetron and at least one substance selected from the group consisting of Alosetron, Ondansetron, Granisetron, Bemesetron and combinations thereof.

9. The method of claim 1, wherein said $5HT_3$-receptor-antagonist is administered intravenously.

* * * * *